United States Patent [19]
Okada et al.

[11] 3,946,727
[45] Mar. 30, 1976

[54] FLEXIBLE TUBE ASSEMBLY FOR AN ENDOSCOPE

[75] Inventors: Takeshi Okada; Katsuyuki Kanehira, both of Tokyo, Japan

[73] Assignee: Olympus Optical Co., Ltd., Tokyo, Japan

[22] Filed: July 11, 1972

[21] Appl. No.: 270,627

[30] Foreign Application Priority Data
June 15, 1971  Japan.............................. 46-62736

[52] U.S. Cl......................................... 128/4; 128/6
[51] Int. Cl.² ........................................... A61B 1/06
[58] Field of Search........... 128/348, 2 M, 2 R, 4, 6, 128/8, 349 R, 350 R

[56] References Cited
UNITED STATES PATENTS

| | | | |
|---|---|---|---|
| 3,485,234 | 12/1969 | Stevens............................ | 128/348 X |
| 3,598,127 | 8/1971 | Wepsic............................ | 128/349 R |
| 3,618,614 | 11/1971 | Flynn................................ | 128/348 |
| 3,670,721 | 6/1972 | Fukami................................ | 128/6 |

*Primary Examiner*—Aldrich F. Medbery
*Attorney, Agent, or Firm*—Kemon, Palmer & Estabrook

[57] ABSTRACT

A flexible tube assembly for an endoscope consisting of a core tube formed by spirally winding an elastic metal band with a layer of material little permeable to X-rays coated on said core tube and a flexible sheath concentrically surrounding said core tube.

1 Claim, 4 Drawing Figures

FLEXIBLE TUBE ASSEMBLY FOR AN ENDOSCOPE

BACKGROUND OF THE INVENTION

This invention relates to a flexible tube assembly for an endoscope and more particularly to a type adapted for medical treatment by emitting X-rays in conjunction with diagnosis by the endoscope. An endoscope for observing and photographing the inner walls of the body cavity consists of an observation section positioned at the forward end of a flexible tube assembly inserted into the body cavity and a control section fitted to the rear end of said flexible tube assembly exposed outside of the body and provided with an eyepiece for observation. The flexible tube assembly further includes a glass fiber member for image transmission, another glass fiber member for illumination of affected parts of the body, a passageway through which to conduct a clamp, an angle wire for allowing the bending of the forward end portion of said flexible tube assembly and a flexible sheath concentrically surrounding the core tube.

Where observation is made of the inner walls of the body cavity, the flexible tube assembly is inserted thereinto and light is emitted through the illumination glass fiber member to light up affected parts being observed. Reflections from the affected parts pass through an observation window, object lens and image transmission glass fiber member to concentrate the image of said affected parts at the rear end face of the glass fiber member. Said image is observed through the object lens of an eyepiece.

Such is the general application of an endoscope. In recent years, however, there has come to be practised medical treatment by emitting X-rays in conjunction with diagnosis by the endoscope. Where X-rays are irradiated to affected parts, the forward end portion of the flexible tube assembly inserted into the body is naturally exposed to said X-rays. At this time, the glass fiber members included in the flexible tube assembly are stained yellow by X-rays, resulting in a prominent decrease in their transparency.

It is accordingly the object of this invention to provide a flexible tube assembly for an endoscope capable of preventing the glass fiber members from being stained yellow by X-rays even when they are emitted in conjunction with the observation of the body cavity walls.

SUMMARY OF THE INVENTION

A flexible tube assembly for an endoscope according to this invention chiefly consists of a core tube formed by spirally winding an elastic metal band and a layer of material little permeable to X-rays coated on the inner and/or outer surface of said core tube. The core tube is further concentrically surrounded with a flexible sheath in close fit.

DETAILED DESCRIPTION OF THE INVENTION

Figure 1:
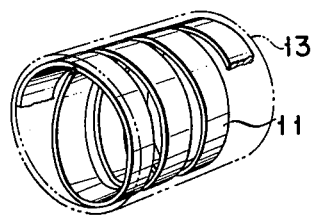
FIG. 1 is a perspective view of a core tube included in a flexible tube assembly for an endoscope according to this invention.

A flexible tube assembly for an endoscope according to this invention has a core tube 11 formed, as illustrated in FIG. 1, by spirally winding an elastic metal band. Said core tube is tightly surrounded with a flexible sheath 13, for example, a synthetic resin pipe in concentric relationship. To render the flexible tube assembly of the aforesaid construction little permeable to X-rays, it may be deemed advisable to prepare the core tube itself from a material prominently resistant to the passage of X-rays. However, a core tube formed by spirally winding a band of lead is quite destitute of elasticity, failing to play the role of a core tube. According to the flexible tube assembly of this invention, therefore, X-rays are shut off by coating the elastic core tube 11 with a layer of material little permeable to X-rays such as lead, oxides thereof, cerium or oxides thereof.

Figure 2:
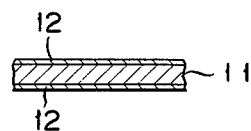
FIG. 2 is a cross sectional view of a spirally wound metal band constituting the core tube coated on both sides with a layer of material little permeable to X-rays.
Figure 3:
FIG. 3 is a cross sectional view of said metal band coated on the inside with said layer of material little permeable to X-rays.
Figure 4:
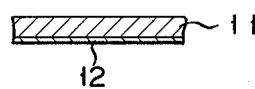
FIG. 4 is a cross sectional view of said metal band coated on the outside with said layer of material little permeable to X-rays.

According to the embodiment of FIG. 2, the core tube 11 made of elastic metal is coated on both inside and outside with a layer 12 strongly resistant to the passage of X-rays. However, said layer 12 may be applied, as shown in FIGS. 3 and 4, either on the outside or the inside alone. Attachment of the layer 12 may be effected by any means, for example, plating the layer material on the core metal, dipping the core metal in molten X-ray obstructing material, or cementing together both core metal and separately provided layer material.

An X-ray obstructing layer thus attached to the core tube 11 of the flexible tube assembly prevents the glass fiber members provided in said assembly from being stained yellow and keeps them sufficiently transparent, enabling the free observation of the body cavity.

What we claim is:

1. A flexible tube assembly for an endoscope comprising a tubular, flexible core formed of a spiral winding of elastic metal strip, said metal strip having coated upon both the inner and outer surfaces a layer of X-ray opaque material and a flexible sheath concentrically surrounding said tubular core in close fit.

* * * * *

UNITED STATES PATENT OFFICE
CERTIFICATE OF CORRECTION

PATENT NO. : 3,946,727
DATED : March 30, 1976
INVENTOR(S) : Takeshi OKADA & Katsuyuki KANEHIRA It is certified that error appears in the above-identified patent and that said Letters Patent are hereby corrected as shown below:

In item [30] June 15, 1971 Japan.....46-62736 should read:

July 15, 1971 Japan.....62236/71

Signed and Sealed this

Seventeenth Day of August 1976

[SEAL]

Attest:

RUTH C. MASON
Attesting Officer

C. MARSHALL DANN
Commissioner of Patents and Trademarks